(12) United States Patent
Feaster

(10) Patent No.: US 6,497,712 B1
(45) Date of Patent: Dec. 24, 2002

(54) KERATOTOMY SURGERY KNIFE

(76) Inventor: Fred T. Feaster, One Beach Dr. South East, Apt. No. 2602, St. Petersburg, FL (US) 33701

( * ) Notice: Subject to any disclaimer, the term of this patent is extended or adjusted under 35 U.S.C. 154(b) by 0 days.

(21) Appl. No.: 09/503,433

(22) Filed: Feb. 14, 2000

(51) Int. Cl.[7] .............................................. A61B 17/32
(52) U.S. Cl. ..................................................... 606/166
(58) Field of Search ........................... 606/1, 166, 167, 606/181; 30/286, 287, 346, 346.55, 346.56, 357, 299

(56) References Cited

U.S. PATENT DOCUMENTS

| | | | |
|---|---|---|---|
| 519,251 A | 5/1894 | Feneran et al. | |
| 561,860 A | 6/1896 | Bringham | |
| 2,215,125 A | * 9/1940 | Maltz | 606/167 |
| 2,706,482 A | * 4/1955 | Griffitts | 606/181 |
| 2,864,370 A | 12/1958 | Alvos | |
| 3,966,350 A | 6/1976 | Benjamin | |
| 4,411,320 A | 10/1983 | Hass | |
| 5,224,950 A | 7/1993 | Prywes | |
| 5,336,235 A | 8/1994 | Myers | |
| 5,370,652 A | * 12/1994 | Kellan | 606/166 |
| 5,433,561 A | 7/1995 | Schimke | |
| 5,554,137 A | 9/1996 | Young et al. | |
| 5,571,124 A | 11/1996 | Zelman | |
| 5,700,274 A | 12/1997 | Feaster | |
| 5,713,915 A | 2/1998 | Van Heugten et al. | |
| 5,810,857 A | * 9/1998 | Mackool | 606/167 |

* cited by examiner

Primary Examiner—Michael H. Thaler
(74) Attorney, Agent, or Firm—Arthur F Zobal

(57) ABSTRACT

The knife has a handle with a blade attached to one end of the handle. The blade has two opposite sides and two edges extending from the handle to a forward cutting edge portion. The two edges are blunt and are non-cutting edges. In one embodiment, the forward cutting edge portion is formed by a pointed inverted V shaped cutting edge extending forward of two outwardly extending straight cutting edges on opposite sides of the base of the pointed inverted V shaped cutting edge with the point of the pointed inverted V shaped cutting edge being located along the centerline of the blade. The outwardly extending cutting edges are transverse to the centerline. In another embodiment, the cutting edge portion is formed by a first edge portion transverse the centerline of the blade and an angled portion located next to one of the non-cutting edges. The angled portion forms an obtuse angle relative to the first edge portion and which extends forward of the first edge portion.

18 Claims, 4 Drawing Sheets

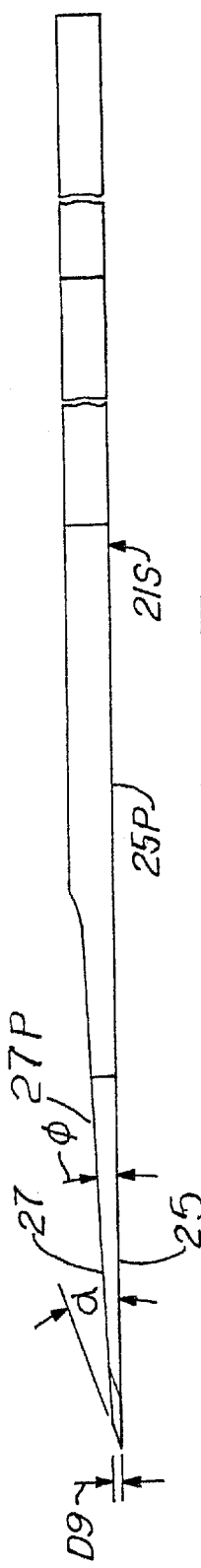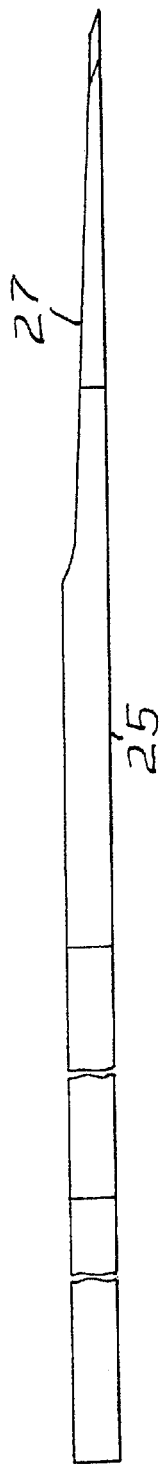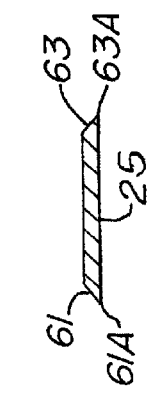
Fig. 3
Fig. 4
Fig. 5
Fig. 6

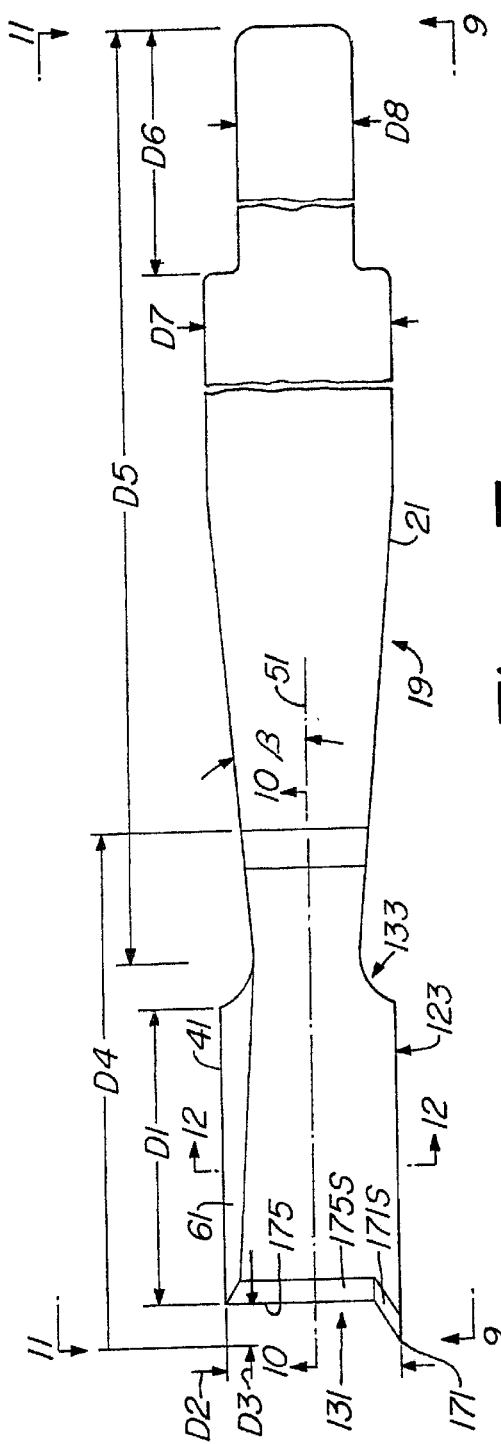
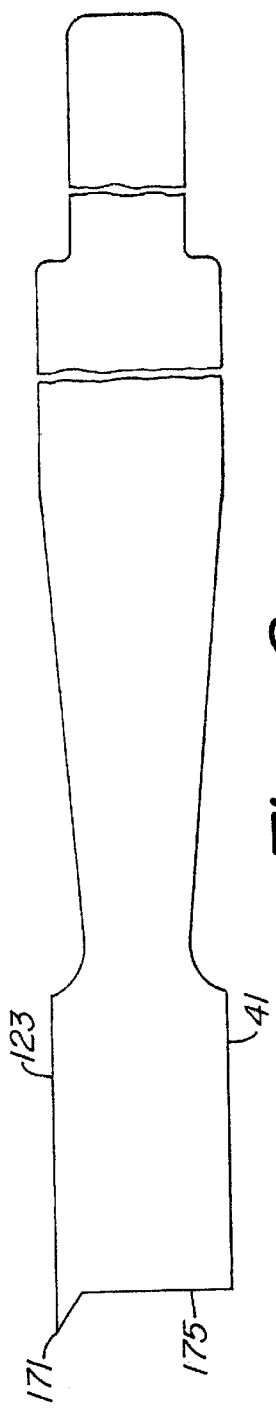
Fig. 7
Fig. 8

KERATOTOMY SURGERY KNIFE

BACKGROUND OF THE INVENTION

1. Field of the Invention

The invention relates to a knife for cataract surgery.

2. Description of the Prior Art

Over the years, the incision in cataract surgery has become progressively smaller. Whereas in the past the larger cataract incisions were created using a combination of a knife and scissors, current cataract incisions can be made solely with the use of a keratotomy knife which in common surgical techniques creates an incision from approximately 2.5 to 3.5 mm in width. Incisions are made in a variety of techniques and locations including. 1). Scleral tunnel in which a partial thickness Scleral incision is made approximately 2 mm posterior to the corneosceral junction, and is dissected anteriorly into clear cornea where the anterior chamber is entered using a sharp tipped keratotomy knife. 2). A limbal—"near clear" which is begun at the corneoscleral junction and carried into clear cornea where again the anterior chamber is entered using a sharp keratotomy knife. 3). Clear corneal incision—in which the cornea is entered anterior to the cornea-scleral junction so that only clear cornea is involved in the incision structure. Again the anterior chamber is entered using a sharp pointed keratotomy knife.

All of these incisions have several characteristics in common. First, they are relatively small, both in width and length. Secondly, all incisions end by entering the anterior chamber through clear cornea. Because these incisions are small, they can be created so that they are self-sealing and do not require suturing. Since they are intended and expected to be self-sealing and water tight to prevent leakage of fluid from the anterior chamber of the eye, it is critical that a reliable, repeatable and appropriately shaped incision be made to prevent vision threatening post-operative complications associated with wound leakage such as infection, and hypotony.

The current commonly used keratotomy blade configurations incorporate certain design characteristics which can result in a less than desirable, and less than ideal incision which may leak due to poor architecture in its creation. More specifically, the common sharp tipped keratotomy does not routinely create, an entry sight into the anterior chamber in a linear fashion, but can cause the incision to extend inadvertently posteriorly toward the limbus thereby creating a less than ideal floor to the incision which may not seal, and may allow aqueous leakage. This posterior extension of the incision is caused by the fundamental design characteristics of the blade tip, and is to a considerable extent independent of surgical expertise in using the blade. Therefore, using this particular blade design, a certain percentage of the incisions will leak due to poor wound architecture from extension of the wound posteriorly.

Another problem with current keratotomy blade designs is that they can inadvertently create a wider than desired incision if the blade is introduced or removed from the incision in a sideways fashion that is not parallel to the original axis of the incision thereby enlarging the wound due to the sharp edges of the sides of the blades. This inadvertent widening of the wound will create a larger wound that leaks not only postoperatively, but intra-operatively during cataract extraction particularly with phaco emulsification where the wound is larger than the phaco emulsification tip thereby allowing egress or outflow of fluid around the tip to an undesirable degree. In modern cataract surgery with phaco emulsification, this fluid egress is a problem since it is desirable to have the wound be water tight during phaco emulsification so that control of the intraocular structures can be maintained throughout the procedure in a more precise fashion. Any leakage around the phaco tip is undesirable. Therefore as can be seen and as is described above, current existing cataract incision knives (keratotomy knives) do not routinely and reliably create ideal water tight self-sealing incisions.

SUMMARY OF THE INVENTION

It is an object of the invention to provide new keratotomy knife tip designs that eliminate the above described problems of inadvertent posterior extension of the wound, and inadvertent widening of the wound. The knife design of one embodiment (FIGS. 1–6) has a sharp central tip that extends backward only a short distance at which point it encounters a redirection of the sharp cutting blade at the "shoulder". By redirecting the sharp cutting edge from a backward to a sideways oriented direction, the cutting edge creates an incision that is essentially linear and parallel to the limbus thereby eliminating the possibility of posterior extension of the wound. Additionally, the side edges of the blade that extend backward from the redirected—horizontal cutting edge, are blunt. By making the side edges of the blade blunt, no cutting or enlarging of the width of the wound will occur, thereby preventing inadvertent enlargement of the wound width if the blade is not introduced or withdrawn in a direction that is absolutely parallel to the incision axis. Therefore, with the keratotomy knife tip configuration here presented, posterior extension of the wound is completely eliminated as is inadvertent enlarging of the wound width. Also, the sharp cutting edges will possibly have a bevel to facilitate their introduction into the anterior chamber with minimal force and maximum smoothness and accuracy, A second embodiment, (FIGS. 7–12) comprises a keratotomy knife with a penetrating sharp cutting tip point with the cutting edge located on the more central side of the blade again extending backwards a short distance at which point the "shoulder" redirects the cutting blade again in a direction almost perpendicular to the direction of introduction into tissue. The side edges of this blade are similarly blunt and unable to cut tissue. This knife tip configuration allows for entry into the anterior chamber through the corneal tissue at the point of the tip and allows is a posterior, backward extension of the incision for only a very short distance at which point the cutting is abruptly redirected in a direction essentially parallel to the limbus. This design characteristic will completely eliminate the undesired posterior extension of the wound toward the limbus during cutting. Since the side edges again are blunt, the wound cannot be inadvertently enlarged by introducing or withdrawing the knife in a direction not parallel to the incision axis.

Therefore, the two herein disclosed keratotomy knife tip configurations both have the design characteristics of eliminating undesirable posterior extension of the wound, and inadvertent widening of the wound thereby more reliably creating self-sealing incisions.

An additional desirable feature of these keratotomy tip designs relates to surgical technique. It is common practice by many surgeons to initiate the incision making process by creating a partial thickness cut-down into the corneal or scleral tissue. After the partial thickness corneal, corneal or scleral cut-down is made, a tunnel is dissected anteriorly to eventually arrive in the clear cornea at which point the anterior chamber is entered. The depth of the initial cutdown is somewhat variable and subject to surgical skill and experience. When using the keratotomy knife tip designs disclosed here, the problem of variability of the depth of the cut down can be eliminated in the following way: The knife tip is introduced perpendicular to the ocular surface and pressed into the tissue cutting until the "shoulder or shoulders" of the blade are reached. Once the shoulders have been barely introduced into the tissue, the blade is then redirected in a forward fashion creating a tunnel of the desired depth, the depth being accuratley and reproducibly established by the distance between the sharp tipped point, and the shoulder. By using the distance between the tip of the keratotomy knife which is first introduced into the tissues, and the shoulders as the final judge for depth of introduction of the blade into the tissues, a reliable depth for introduction of the blade is created, the distance between the tip and shoulders acting as a reliable gauge for depth of penetration of the blade into the tissues. Once the depth of penetration of the blade tip into the tissues has reached the level of the shoulder, the blade is redirected so that the blade is in a plane almost parallel to the iris. With the knife in this orientation, the tunnel is created by pushing the blade forward into the clear cornea to the desired extent after which time the blade tip is redirected again toward the anterior chamber where the last deep layers of cornea including the endothelium are penetrated and cut leaving a linear incision in the endothelium that is virtually parallel to the limbus with no posterior extension. The blunt blade sides will prevent inadvertent enlargement of the wound even with inadvertent side to side movement of the knife during reorientation of the blade during the incision process. This is true of both the center point tip configuration, and the side point configuration.

BRIEF DESCRIPTION OF THE DRAWINGS

FIG. 3 is an edge view of the knife of FIG. 1 as seen along lines 3—3 thereof.

FIG. 4 is an edge view of the knife of FIG. 1 as seen along lines 4—4 thereof.

FIG. 5 is an edge view of FIG. 1 as seen along lines 5—5 thereof.

FIG. 6 is a cross-section of FIG. 1 as seen along lines 6—6 thereof.

FIG. 7 is a plan view of one side of a knife of another embodiment of the invention.

FIG. 8 is a plan view of a side of the knife of FIG. 7 opposite that of FIG. 7.

DESCRIPTION OF THE PREFERRED EMBODIMENTS

Figure 1:
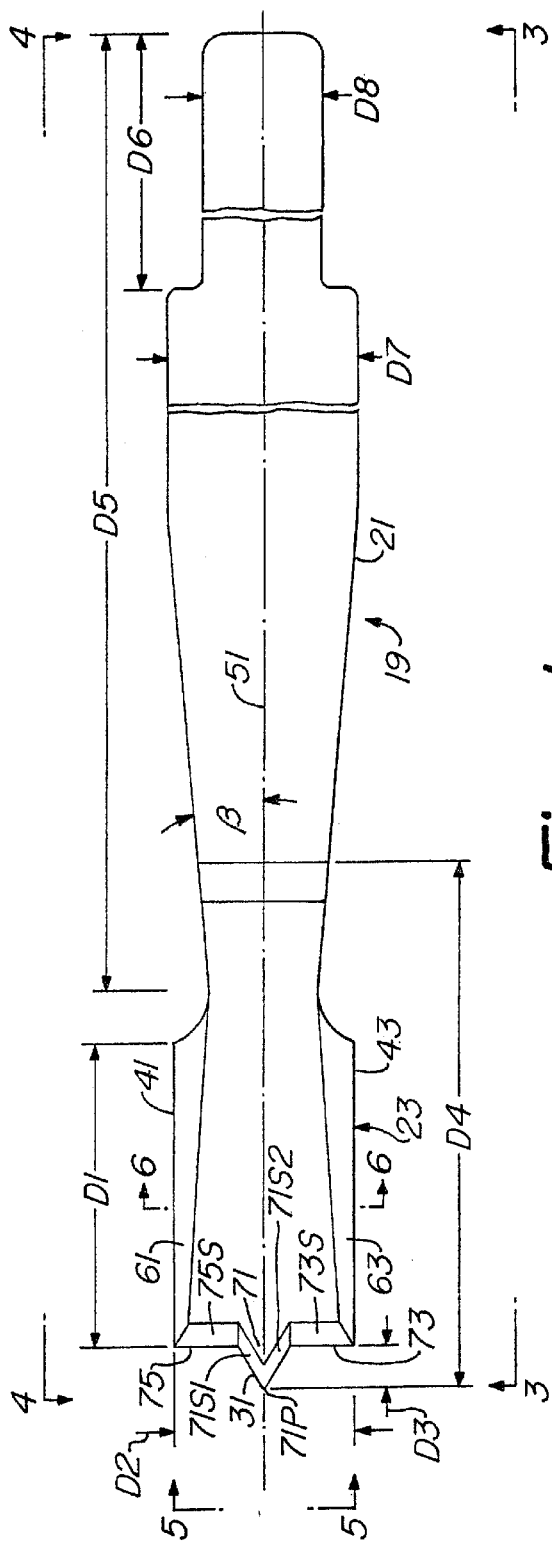
FIG. 1 is a plan view of one side of the knife of one embodiment of the invention.
Figure 2:
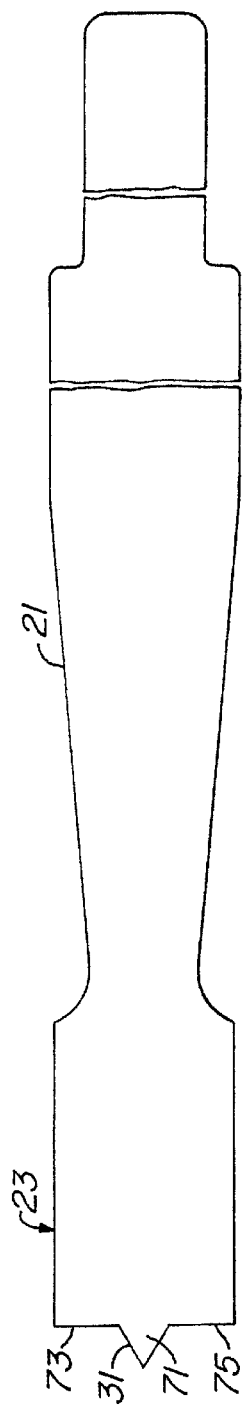
FIG. 2 is a plan view of a side of the knife of FIG. 1 opposite that of FIG. 1.

Referring to FIGS. 1–6, the knife 19 shown comprises a handle 21 having a blade 23 coupled to one end thereof. The blade 23 comprises a first flat side 25 in a first plane 25P and a second flat side 27 in a second plane 27P. The handle 21 has a side 21S in the plane 25P. The two sides 25 and 27 extend from the handle 21 to a cutting edge portion 31. The two sides 25 and 27 define a small acute angle $\phi$ from the cutting edge portion 31 to the handle 21. The angle $\phi$ may be of the order of 2° 29'. The blade 23 has two side edges 41 and 43 which are on opposite sides of the center line 51 and which are blunt or non-cutting edges. The angles $\gamma$ formed by the surfaces 61 and 63 with the flat side 25 each is of the order of 30°. Although not shown, the junctures of the surfaces 61 and 63 with the surface 25 at 61A(see FIGS. 1, 5, and 6) may be rounded or blunted to prevent cutting action.

The cutting edge portion 31 comprises a pointed inverted V shaped cutting edge 71 extending forward of two straight cutting edges 73 and 75 extending outwardly sideways from the base of the pointed inverted V shaped cutting edge 71 with the point 71P of the pointed inverted V shaped cutting edge being located along the centerline 51. The cutting edges 73 and 75 are perpendicular to the centerline 51. The pointed inverted V shaped cutting edge 71 and the two shoulder cutting edges 73 and 75 are defined by surfaces 71S1, 71S2, 73S and 75S which extend from the plane 25P to the plane 27P and which form second acute angles $\alpha$ greater than $\phi$. The angles $\alpha$ may be of the order of 18°.

The handle 21 may be formed of metal and the blade 23 may be formed of diamond, metal or other suitable material capable of holding a sharp edge and which is attached to the handle by suitable means. In one embodiment, the dimensions shown may be as follows. D1=4.522 mm; D2=2.6 mm; D3=0.660 mm; D4=7.8 mm; D5=0.947 cm; D6=0.312 cm; D7=0.11 cm; D8=0.0710 cm; D9=0.102 mm. The $\beta$ may be equal to 5°. It is to be understood that the angles and dimensions listed. above may vary somewhat however the angles $\alpha$ will always result in sharp cutting edges and will be greater than $\phi$ and the angles $\gamma$ will be large enough to result in side edges 41 and 43 being blunt or forming non-cutting edges. The two surfaces 25 and 27 (see FIG. 3) may be parallel to each other whereby $\phi$ will be equal to zero.

Figure 9:
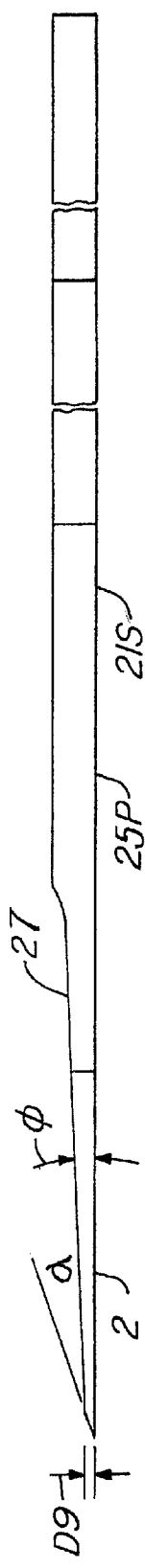
FIG. 9 is an edge view of the knife of FIG. 7 as seen along lines 9—9 thereof.
Figure 10:
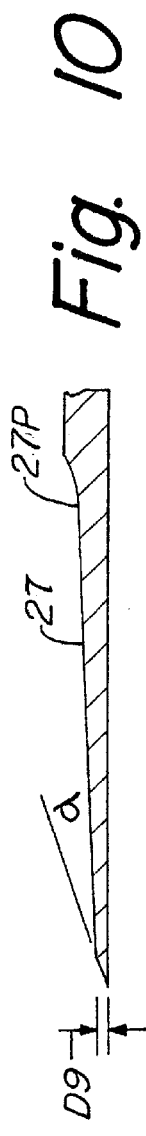
FIG. 10 is a partial edge view of the knife of FIG. 7 as seen along lines 10—10 thereof.
Figure 11:
FIG. 11 is an edge view of FIG. 7 as seen along lines 11—11 thereof.
Figure 12:
FIG. 12 is a cross-sectional view of FIG. 7 as seen along lines 12—12 thereof.

Referring to FIGS. 7–12, the embodiment shown is the same as that of FIGS. 1–6 except for the blade 133. In FIGS. 7–12 like-reference numerals identify the same elements as identified in FIGS. 1–6 and in FIGS. 7–12 the dimensions D1, D2, D3, D4, D5, D6, D7, D8 and D9 and angles $\alpha$, $\phi$, $\gamma$ and $\beta$ are the same as those referred to in FIGS. 1–6. In FIGS. 7–12, the side edge 123 is blunt and is perpendicular to the plane 25P. The cutting portion 131 comprises a pointed blade 171 on one side of the center line 51 and a cutting edge 175 extends from the cutting edge 171 to the side 41. The cutting edge 175 is perpendicular to the center line 51. The surfaces 171S and 175S form angles $\alpha$ from the flat side 25 to the flat side 27 equal to about 18°. Although not shown, the juncture of the surface 61 with the surface 25 at 61A(see FIGS. 7 and 12) may be rounded or blunted to prevent cutting order of 30°. Although not shown, the junctures of the surfaces 61 and 63 with the surface 27 at 61A and 63B(see FIGS. 1, 5, and 6) may be rounded or blunted to prevent cutting action.

The cutting edge portion 31 comprises a pointed inverted V shaped cutting edge 71 extending forward of two straight cutting edges 73 and 75 extending outwardly sideways from the base of the pointed inverted V shaped cutting edge 71 with the point 71P of the pointed inverted V shaped cutting edge being located along the centerline 51. The cutting edges 73 and 75 are perpendicular to the centerline 51. The pointed inverted V shaped cutting edge 71 and the two shoulder cutting edges 73 and 75 are defined by surfaces 71S1, 71S2, and 75S which extend from the plane 25P to the plane 27P and which form second acute angles α greater than ϕ. The angles α may be of the order of 18°.

The handle 21 may be formed of metal and the blade 23 may be formed of diamond, metal or other suitable material capable of holding a sharp edge and which is attached to the handle by suitable means. In one embodiment, the dimensions shown may be as follows. D1=4.52 mm; D2=2.6 mm; D3=0.660 mm; D4=7.8 mm; D5=0.947 cm; D6=0.312 cm; D7=0.1 cm; D8=0.071 cm; D9=0.102 mm. The β may be equal to 5°. It is to be understood that the angles and dimensions listed above may vary somewhat however the angles a will always result in sharp cutting edges and will be greater than α and the angles γ will be large enough to result in side edges 41 and 43 being blunt or forming non-cutting edges. The two surfaces 25 and 27 (see FIG. 3) may be parallel to each other whereby ϕ will be equal to zero.

Referring to FIGS. 7–12, the embodiment shown is the same as that of FIGS. 1–6 except for the blade 133. In FIGS. 7–12 like reference numerals identify the same elements as identified in FIGS. 1–6 and in FIGS. 7–12 the dimensions D1, D2, D3, D4, D5, D6, D7, D8 and D9 and angles α, ϕ, γ and β are the same as those referred to in FIGS. 1–6. In FIGS. 7–12, the side edge 123 is blunt and is perpendicular to the plane 25P. The cutting portion 131 comprises a pointed blade 171 on one side of the center line 51 and a cutting edge 175 extends from the cutting edge 171 to the side 41. The cutting edge 175 is perpendicular to the center line 51. The surfaces 171S and 175S form angles α from the flat side 25 to the flat side 27 equal to about 18°. Although not shown, the juncture of the surface 61 with the surface 27 at 61 A(see FIGS. 7 and 12) may be rounded or blunted to prevent cutting

What is claimed is:

1. A keratotomy surgery knife, comprising:

a handle having a blade at one end, said blade comprising a first flat side in a first plane and an opposite second flat side in a second plane, which extend to a forward cutting edge portion, said blade having first and second opposite non-cutting edges on opposite sides of a centerline extending to said forward cutting edge portion, said cutting edge portion comprising a first edge portion transverse to said centerline and an angled portion which forms an obtuse angle relative to said first edge portion, said angled portion comprises a forwarded extending member located closer to one of said non-cutting edges than to the other of said non-cutting edges, said angled portion and said first edge portion being defined by surfaces which extend from said first plane to said second plane and which form acute angles relative to said second flat side.

2. The knife of claim 1, wherein:

said first edge portion is straight, and said angled portion is straight.

3. The knife of claim 2, wherein:

said first edge portion is perpendicular to said center line.

4. The knife of claim 3, wherein:

said blade and said handle are fixed together as an integral member.

5. The knife of claim 4, wherein:

said first and second flat sides define an acute angle which is less than said acute angles formed by said surfaces of said angled portion and said first edge portion.

6. The knife of claim 3, wherein:

said first and second flat sides define an acute angle which is less than said acute angles formed by said surfaces of said angled portion and said first edge portion.

7. The knife of claim 2, wherein: said blade and said handle are fixed together as an integral member.

8. The knife of claim 2, wherein:

said first and second flat sides define an acute angle which is less than said acute angles formed by said surfaces of said angled portion and said first edge portion.

9. The knife of claim 1, wherein:

said first edge portion is perpendicular to said center line.

10. The knife of claim 1, wherein:

said blade and said handle are fixed together as an integral member.

11. The knife of claim 10, wherein:

said first and second flat sides define an acute angle which is less than said acute angles formed by said surfaces of said angled portion and said first edge portion.

12. The knife of claim 1, wherein:

said first and second flat sides define an acute angle which is less than said acute angles formed by said surfaces of said angled portion and said first edge portion.

13. A keratotomy surgery knife, comprising:

a handle having a blade at one end, said blade comprising a first flat side in a first plane and an opposite second flat side in a second plane, extending from said handle to a forward cutting edge portion, said first and second flat sides define a first acute angle extending from said forward cutting edge portion to said handle, said blade having first and second opposite non-cutting edges on opposite sides of a centerline extending from said handle to said forward cutting edge portion, said forward cutting edge portion comprising a pointed inverted V shaped cutting edge extending forward of two straight aligned cutting edges located on opposite sides of the base of said pointed inverted V shaped cutting edge with the point of said pointed inverted V shaped cutting edge being located along said centerline, said pointed inverted V shaped cutting edge and said two outwardly extending cutting edges being defined by surfaces which extend from said first plane to said second plane and which form second acute angles relative to said second flat side greater than said first acute angle.

14. A keratotomy surgery knife, comprising:

a handle having a blade at one end, said blade comprising a first flat side in a first plane and an opposite second flat side in a second plane, extending from said handle to a forward cutting edge portion, said blade having first and second opposite non-cutting edges on opposite sides of a centerline extending from said handle to said forward cutting edge portion, said cutting edge portion comprising a first edge portion transverse to said centerline and an angled portion which forms an obtuse angle relative to said first edge portion, said angled portion and said first edge portion being defined by surfaces which extend from said first plane to said second plane and which form acute angles relative to said second flat side, said angled portion comprises a forward extending member located completely on one side of said centerline and next to one of said non-cutting edges.

15. The keratotomy surgery knife, comprising:

a handle having a blade at one end, said blade comprising a first flat side in a first plane and an opposite second flat side in a second plane, which extend to a forward cutting edge portion, said blade having first and second opposite non-cutting edges on opposite sides of a centerline extending to said forward cutting edge portion, said cutting edge portion comprising a pointed V-shaped cutting member having a forward extending point and two angled cutting edges extending forward to said point from two aligned cutting edges which are transverse to said centerline and which are located on opposite sides of said V-shaped cutting member, each of said two angled cutting edges and said two aligned cutting edges being defined by surfaces which extend from said first plane to said second plane and which form acute angles relative to said second flat side, said first and second flat sides define an acute angle which is less than said acute angles formed by said surfaces of said angled portion and said first edge portion.

16. The knife of claim 15, wherein:

said two aligned cutting edges are straight, and said two angled cutting edges are straight.

17. The knife of claim 15, wherein:

said two aligned cutting edges are perpendicular to said centerline.

18. The knife of claim 15, wherein:

said blade and said handle are fixed together as an integral member.

* * * * *